(12) United States Patent
Lally

(10) Patent No.: US 9,078,884 B2
(45) Date of Patent: Jul. 14, 2015

(54) BIO-MATERIAL COMPOSITION AND METHOD FOR SPINAL FUSION

(71) Applicant: Thomas Joseph Lally, Oak Brook, IL (US)

(72) Inventor: Thomas Joseph Lally, Oak Brook, IL (US)

(*) Notice: Subject to any disclaimer, the term of this patent is extended or adjusted under 35 U.S.C. 154(b) by 155 days.

(21) Appl. No.: 13/842,972

(22) Filed: Mar. 15, 2013

(65) Prior Publication Data

US 2013/0216629 A1   Aug. 22, 2013

Related U.S. Application Data

(63) Continuation-in-part of application No. 13/244,533, filed on Sep. 25, 2011, now abandoned, which is a continuation-in-part of application No. 11/813,365, filed as application No. PCT/US2006/000968 on Jan. 12, 2006, now abandoned, said application No. 13/244,533 is a continuation-in-part of application No. 11/575,590, filed as application No. PCT/US2005/034035 on Sep. 21, 2005, now abandoned.

(60) Provisional application No. 61/686,448, filed on Apr. 5, 2012, provisional application No. 60/643,312, filed on Jan. 12, 2005, provisional application No. 60/611,840, filed on Sep. 21, 2004.

(51) Int. Cl.
| | |
|---|---|
| A61L 27/54 | (2006.01) |
| A61K 33/42 | (2006.01) |
| A61K 33/08 | (2006.01) |
| A61L 27/12 | (2006.01) |

(52) U.S. Cl.
CPC ............... *A61K 33/42* (2013.01); *A61K 33/08* (2013.01); *A61L 27/12* (2013.01); *A61L 27/54* (2013.01); *A61L 2300/414* (2013.01); *A61L 2430/38* (2013.01)

(58) Field of Classification Search
None
See application file for complete search history.

(56) References Cited

U.S. PATENT DOCUMENTS

| | | | |
|---|---|---|---|
| 5,942,499 A | 8/1999 | Radomsky | |
| 6,331,312 B1 | 12/2001 | Lee et al. | |
| 6,533,821 B1 | 3/2003 | Lally | |
| 6,733,582 B1 | 5/2004 | Bohner et al. | |
| 6,787,495 B2 | 9/2004 | Lally | |
| 2003/0199615 A1 | 10/2003 | Chaput et al. | |
| 2004/0034428 A1* | 2/2004 | McKay | 623/17.16 |
| 2005/0031704 A1 | 2/2005 | Ahn | |
| 2007/0218144 A1 | 9/2007 | Lally | |
| 2008/0119859 A1* | 5/2008 | Lally | 606/76 |
| 2010/0034898 A1 | 2/2010 | Lally | |
| 2010/0092573 A1 | 4/2010 | Lally | |
| 2012/0141596 A1 | 6/2012 | Lally | |
| 2012/0308552 A1 | 12/2012 | Lally | |

FOREIGN PATENT DOCUMENTS

| | | |
|---|---|---|
| WO | 01/41822 A1 | 6/2001 |
| WO | 01/97679 | 12/2001 |
| WO | 2006/076426 | 7/2006 |

OTHER PUBLICATIONS

PCT International Application Search Report PCT/US2006/00968, dated Jul. 18, 2007.
PCT International Application Search Report PCT/US2005/34035, dated Jun. 5, 2007.
Supplemental European Search Report for EU Patent Application No. 05798295.1, which is a EU national phase application of PCT/US2005/34035.

* cited by examiner

*Primary Examiner* — Carlos Azpuru
*Assistant Examiner* — Casey Hagopian

(57) ABSTRACT

The present invention relates to a material and method for providing spinal fusion. One preferred method comprises: accessing the intervertebral space defined between adjacent vertebrae; mixing magnesia, potassium biphosphate, and a calcium phosphate with an aqueous solution forming an activated spinal fusion slurry (ASFS); applying an effective amount of the ASFS to the intervertebral space between adjacent vertebrae; allowing the ASFS to set forming a bonded vertebrae structure; permitting bone growth into the bonded vertebrae structure providing fusion of the two adjacent vertebrae.

19 Claims, No Drawings

BIO-MATERIAL COMPOSITION AND METHOD FOR SPINAL FUSION

RELATION TO OTHER APPLICATIONS

The present application is a non-provisional application of, and claims priority to, U.S. provisional patent application No. 61/686,448, filed on Apr. 5, 2012, and is also continuation-in-part of, and seeks priority to pending U.S. patent application Ser. No. 13/244,533, filed on Sep. 25, 2011, which is a continuation-in-part of, and seeks priority to, U.S. patent application Ser. No. 11/813,365 filed on Jul. 5, 2007, which is a national stage application and claims priority to PCTUS2006/000968, filed on Jan. 12, 2006, which claims priority to U.S. provisional application No. 60/643,312 filed on Jan. 12, 2005, the present application is also a continuation-in-part application of and claims priority to U.S. patent application Ser. No. 11/575,590, filed on Mar. 20, 2007 which is a national stage application of PCT/US2005/34035 filed on Sep. 21, 2005, which claims priority of U.S. provisional application No. 60/611,840 filed on Sep. 21, 2004, all of which are hereby incorporated by reference in their entireties.

TECHNICAL FIELD

The present invention relates to a composition and method for promoting spinal fusion. One or more preferred embodiments provide a replacement and/or supplement to for other spinal fusion biomaterials like BMP-2 and IMPDH.

BACKGROUND OF THE INVENTION

Increasing numbers of sports, age, and trauma related injuries like broken bones, worn out joints, and torn ligaments have heightened the demand for bio-materials capable of treating orthopedic injuries. In response, companies have developed bone cements to attach various objects to bone, and bone fillers capable of treating bone fractures and other bone defects. There is also a need for a bio-material capable of stimulating bone formation and growth and a material for providing spinal fusion. Most existing bio-materials are made of calcium phosphates that promote significant new bone formation or relatively inert hardening polymers like polymethylmethcrylate ("PMMA") that are poorly biocompatible and do not promote new bone formation or spinal fusion without the use of additional fixation devices.

A number of calcium phosphate based compositions have been developed as biomaterials in recent years. For example U.S. Pat. No. 6,331,312 issued to Lee et al., discloses an injectable calcium phosphate based composite useful as a bone filler and cement. The disclosed material is bio-resorbable and is designed for use in the repair and growth promotion of bone tissue as well as the attachment of screws, plates and other fixation devices. Lee's composition does not expand while setting and does not promote significant new bone formation, nor provide spinal fusion. Many existing calcium phosphate based fillers and cements have high molar ratios of Ca to P making them poorly reabsorbable. Furthermore, a recent FDA release warns of serious complications from the use of existing calcium phosphate based bone fillers in treating fractures of the spine (FDA Public Health Web Notification, "Complications Related to the Use of Cement and Bone Void Fillers in Treating Compression Fractures of the Spine," originally published Oct. 31, 2002, updated, May 27, 2004.)

Generally, current calcium phosphate cements lack the characteristic of a successful compound for providing spinal fusion. In fact, recent studies have investigated the ability of bone void fillers to provide spinal fusion, however, the results have demonstrated that current bone void fillers do not provide adequate spinal fusion to be successful replacement for current bone fusion inducing biomaterial like IMPDH and BMP-2.

DETAILED DISCLOSURE OF THE INVENTION

The present invention describes a material and method for providing spinal fusion. One preferred embodiment of the invention is a method for fusing two adjacent vertebrae comprising: accessing the intervertebral space defined between adjacent vertebrae; mixing magnesia, potassium biphosphate, and a tricalcium phospahte with an aqueous solution forming an activated spinal fusion slurry (ASFS); applying an effective amount of the ASFS to the intervertebral space between adjacent vertebrae; allowing the ASFS to set forming a bonded vertebrae structure; permitting bone growth into the bonded vertebrae structure providing fusion of the two adjacent vertebrae.

DEFINITIONS

"Osteoconductive" is the ability of material to serves as a scaffold for viable bone growth and healing.

"Osteoinductive" refers to the capacity to stimulate or induce bone growth.

"Biocompatible" refers to a material that elicits no significant undesirable response in the recipient.

"Bioresorbable" is defined as a material's ability to be resorbed in-vivo through bodily processes. The resorbed material may be used the recipients body or may be excreted.

"Prepared Cells" are defined as any preparation of living cells including but not limited to tissues, cell lines, transformed cells, and host cells. The cells are preferably autologous but can also be xenogeneic, allogeneic, and syngeneic.
Preparing/Supplying the Dry Mixture A salient aspect of the invention is the dry mixture. The dry mixture generally comprises: magnesia, potassium biphosphate, and a calcium tricalcium phosphate, wherein the weight percent ratio of potassium biphosphate to magnesia is between about 3:1 and 1:1. In one or more preferred embodiments the dry mixture also comprises a sugar and/or a monosodium phosphate. It may be preferable to produce the dry mixture in advance. After it is prepared it should be stored in a sterile environment and more preferably a sterile and sealed container or packaging.

The dry components of the mixture can be mixed using a variety of methods including hand mixing or machine mixing. One method for mixing, sizing and homogenizing the various powders is via vibratory milling. Another homogenization method utilizes a ribbon mixer wherein the particles are ground to a fine size. It may be preferable to mix the dry components again on-site before the addition of the activating aqueous solution.

Magnesia is a salient ingredient of the invention. Optionally, the magesia is subjected to a calcinated process. Calcination durations and temperatures are determined empirically, depending on the final characteristics and setting times desired. In some embodiments calcination temperatures of up to about 1300° C. for up to several hours are used, although calcination can be varied.

Dry compounds are disclosed herein, however, it may be possible to substitute aqueous versions (or other forms i.e.

gels etc) of the components in certain situations. Generally, pharmaceutical grade compounds are utilized when available.

Sterilization of the components, utensils, solutions etc. used to make and apply the slurry may be required using suitable sterilization techniques known in the art including but not limited to chemical sterilization techniques, such as gassing with ethylene oxide, and sterilization by means of high-energy radiation, usually γ radiation or β radiation.

Details of the dry mixture composition is described below in detail.

Forming an Activated Spinal Slurry

The dry mixture is preferably activated on-site. The supplied dry mixture is mixed with an aqueous solution in a sterile mixing vessel to a form an activated spinal fusion slurry (ASFS). The sterile water (or other sterile aqueous solution i.e. slight saline solution) is generally added up to about 40% of the dry weight although the amount of water can be adjusted to form a bio-material of varying viscosity. In a preferred embodiment, the mixing vessel and utensil are sterilized prior to use. Various mixing vessels can be used including but not limited to a sterile medicine cup, bowl, dish, basin or other sterile container.

The ASFS is typically hand mixed for between about 1-10 minutes, although mixing times can be adjusted depending upon conditions and mixing means. Mixing can be achieved by a variety of techniques used in the art including hand and electric/automated mixing. One preferred method is to hand mix with a sterile spatula or other mixture utensil.

It may be possible to mix the slurry using manual hand mixers like the Mixevac III from Stryker (Kalamzoo, Mich.) or an electric bone mixer like the Cemex Automatic Mixer from Exactech (Gainesville, Fla.).

The ASFS can be created in injectable, paste, puddy and other forms. Since the slurry is produced at the user site the consistency of the material can be manipulated by varying the amount of water added to the dry mixture. Increasing the water content generally increases the flowability while decreasing the water content tends to thicken the slurry.

Working times can be increased or decreased by varying the temperatures of bio-material components. Higher temperature components tend to react and set quicker than cooler components. Thus regulating the temperature of the water (or other reactants) can be an effective way to regulate working time.

The inventor has found that the use of a phosphoric acid instead of water increases the bonding strength of the material. The molarity of the phosphoric acid can vary, as long as the eventual pH of the slurry is not hazardous to the patient, or contraindicative to healing.

Applying the ASFS to the Site

Once the activated slurry has been formed the ASFS is applied to (and optionally also around) the site of desired cartilage growth. The slurry can be applied to the site in a number of ways including but not limited to spreading an amount of the material to the site using a sterile spatula, tongue blade, knife or other sterile implement useful for spreading a paste or puddy-like material. In some situations it may be preferable to use a relatively thick consistency like a paste or puddy when applying the ASFS, since such consistencies tend to stick to bone and other surface more easily than thinner ones. Initial results have indicated that using puddy may be preferable for providing spinal fusion. If an injectable formation is desired, it can be applied using a syringe or other similar device.

Exemplary formulations of the dry mixture include the following:

| Formulation I* | |
|---|---|
| Mono-potassium phosphate (i.e. $KH_2PO_4$) | 61% |
| Magnesia (calcined) | 31% |
| $Ca_{10}(PO_4)_6(OH)_2$ | 4% |
| Sucrose $C_{12}H_{22}O_{11}$ (powder) | 4% |

*All values are weight percentages

Water is added up to about 40 weight percent of the dry formulation, preferably between about 20-35 weight percent.

| Formulation II* | |
|---|---|
| $KH_2PO_4$ | 54% |
| MgO (calcined) | 33% |
| Calcium-containing compound | 9% (whereby the compound is $Ca_{10}(PO_4)_6(OH)_2$) |
| Sucrose $C_{12}H_{22}O_{11}$ (powder) | 4% |

*All values are weight percentages

Water is added up to about 40 weight percent of the dry formulation, preferably between about 20-35 weight percent.

| Formulation III* | |
|---|---|
| $KH_2PO_4$ | 44% |
| MgO (calcined) | 44% |
| Calcium-containing compound | 8% (whereby the compound is $Ca_{10}(PO_4)_6(OH)_2$ or $CaSiO_3$, |
| Sucrose $C_{12}H_{22}O_{11}$ (powder) | 4% |

*All values are weight percentages

Water is added up to about 40 weight percent of the dry formulation, preferably between about 20-35 weight percent.

| Formulation IV* | |
|---|---|
| Potassium phosphate (i.e. $KH_2PO_4$) | 44% |
| MgO (calcined) | 41% |
| $Ca_{10}(PO_4)_6(OH)_2$ | 8% |
| Sucrose $C_{12}H_{22}O_{11}$ (powder) | 4% |
| Mono-sodium phosphate (MSP) | 3% |

*All values are weight percentages

Water is added up to about 40 weight percent of the dry formulation, preferably between about 20-35 weight percent, more preferably between about 28-32 weight percent.

| Formulation V* | |
|---|---|
| $KH_2PO_4$ | 45% |
| MgO (calcined) | 45% |
| Calcium-containing compound | 9% |
| Sucrose $C_{12}H_{22}O_{11}$ (powder) | 1% |

*All values are weight percentages

Water is added up to about 40 weight percent of the dry formulation, preferably between about 20-35 weight percent.

| Formulation VI* | |
| --- | --- |
| $KH_2PO_4$ | 45% |
| MgO (calcined) | 45% |
| $Ca_{10}(PO_4)_6(OH)_2$ | 8% |
| Sucralose | 2% |

*All values are weight percentages

Water is added up to about 40 weight percent of the dry formulation, preferably between 20-35 weight percent.

| Formulation VII* | |
| --- | --- |
| $KH_2PO_4$ | 61% |
| MgO (calcined) | 32% |
| $Ca_{10}(PO_4)_6(OH)_2$ | 4% |
| Collagen | 1.5% |
| $\alpha\text{-}Ca_3(PO_4)_2$ | 1.5% |

*All values are weight percentages

Water is added up to about 40 weight percent of the dry formulation, preferably between 20-35 weight percent.

| Formulation VIII* | |
| --- | --- |
| $KH_2PO_4$ | 50% |
| MgO (calcined) | 35% |
| $Ca_{10}(PO_4)_6(OH)_2$ | 7% |
| $\beta\text{-}Ca_3(PO_4)_2$ | 3% |
| Dextrose | 5 |

*All values are weight percentages

Water is added up to about 40 weight percent of the dry formulation, preferably between 20-35 weight percent.

| Formulation IX* | |
| --- | --- |
| $KH_2PO_4$ | 54% |
| Phosphoric Acid | 4% |
| Metal oxide | 32% (wherein the metal oxide is MgO, ZrO, FeO or combination thereof), |
| $Ca_{10}(PO_4)_8(OH)_2)$ | 7% |
| Thrombin | 3% |

*All values are weight percentages

Water is added up to about 40 weight percent of the dry formulation, preferably between 20-35 weight percent.

| Formulation X* | |
| --- | --- |
| $KH_2PO_4$ | 45% |
| MgO (calcined) | 45% |
| $Ca_{10}(PO_4)_6(OH)_2$ | 10% |

Water is added up to about 40 weight percent of the dry formulation, preferably between 20-35 weight percent.

While the above formulations and weight percents are the preferred proportions, a range of dry constituents can also be used. For example, a suitable range for the potassium biophosphate (i.e. MKP) is generally between about 20-70 weight percent, preferably between about 40-65 weight percent. In some situations and/or embodiments it is preferable to use the potassium phosphate at a range between about 40-50 weight.

A suitable range for the magneisa (i.e. MgO) is generally between about 10-60, preferably between 10-50, and even more preferably between 30-50 weight percent. In some situations and/or embodiments it maybe preferable to use between about 35 and 50 weight percent.

Tricalcium phosphate (preferably a tricalcium apatite) and other calcium phosphates can be added in various weight percentages. The calcium containing compound(s) is/are preferably added at about 1-15 weight percent, more preferably between about 1-10 weight percent. Higher percentages can be employed in certain situations.

Sugars (and/or other carbohydrate containing substances) are generally present at weight percent between 0.5 and 20, preferably about 0.5-10 weight percent of the dry composition.

Typically the antibiotic, antibacterial or antiviral agent is added at a weight percent of less than about 20 weight percent of the dry composition, preferably between about 0.5 and 10 weight percent, more preferably between about 1 and 5 weight percent.

Water (or another aqueous solution) can be added in a large range of weight percents generally ranging from about 15-40 weight percent, preferably between about 20-35 weight percent and even more preferably between about 28-32 weight percent. It was found that a saline solution may be used. An exemplary saline solution is a 0.9% saline solution.

For some embodiments (i.e. formula III) it has been found that adding water at a weight percent of about 37 weight percent produces a creamy textured material that is extremely easy to work with has excellent adhesive properties and is easily injectable through a syringe.

The noted ranges may vary with the addition of various fillers, equivalents and other components or for other reasons.

A salient feature of the present invention is the ratio between MKP (MKP equivalent, combination, and/or replacement) and the metal oxide (i.e. magnesia). A preferred embodiment has a weight percent ratio between MKP and MgO between about 4:1 and 0.5:1, more preferably between approximately 3:1 and 1:1. In such a preferred embodiment the inventor surmises that the un-reacted magnesium is at least partly responsible for the in vivo expandability characteristics of the bio-adhesive.

Specifically the metal oxide (i.e. magnesium oxide) reacts with water and serum and in and around the living tissue to yield $Mg(OH)_2$ and magnesium salts. It has been found that some embodiments of the material generally expand to between 0.15 and 0.20 percent of volume during curing in moisture. The expansion of the material is believed to increase the adhesive characteristics of the material.

Potassium biphosphate (i.e. MKP) is a salient part of the invention. When MKP is utilized inventor has discovered that a sodium phosphate can also be added to the matrix in order to control the release of potentially dangerous ions to make the matrix more bio-compatible. When used for this purpose the sodium phosphate can be added in an amount sufficient to capture the desired amount of ions (i.e. potassium ions). The sodium phosphate (i.e. mono-sodium phosphate) is typically added up top about 20 weight percent, preferably up to about 10 weight percent, and even more preferably up to about 5 weight percent. Other sodium compounds may also prove helpful in this regard.

Tertiary Calcium Phosphate

A tertiary calcium phosphate is essential to one or more embodiments of the invention as it increases both the bio-compatibility and bio-absorption of the biomaterial. Suitable tricalcium phosphates include $\alpha\text{-}Ca_3(PO_4)_2$, $\beta\text{-}Ca_3(PO_4)_2$, and $Ca_{10}(PO_4)_6(OH)_2$. A preferred a tertiary calcium phosphate is a pharmaceutical or food grade tricalcium phosphate manufactured by Astaris (St. Louis, Mo.).

In addition to the tertiary calcium phosphate other calcium containing compounds can be added. In general, suitable calcium containing compounds include but are not limited to: tricalcium phosphates, biphasic calcium phosphate, tetracalcium phosphate, amorphous calcium phosphate ("ACP"), $CaSiO_3$, oxyapatite ("OXA"), poorly crystalline apatite ("PCA"), octocalcium phosphate, dicalcium phosphate, dicalcium phosphate dihydrate, calcium metaphosphate, heptacalcium metaphosphate, calcium pyrophosphate and combinations thereof. Other calcium containing compounds include: ACP, dicalcium phosphate, $CaSiO_3$, dicalcium phosphate dihydrate and combinations thereof.

Calcium containing compounds increase the bio-compatibility and bioabsorption of the bio-adhesive. However, calcium containing compounds vary in their degrees of bioabsorption and biocompatibility. Some characteristics even vary within the various tricalcium phosphate compounds.

It may be advantageous to combine various calcium containing compounds to manipulate the bio-compatibility and bioabsorption characteristics of the material. For example $Ca_{10}(PO_4)_6(OH)_2$ (HA") is stable in physiologic conditions and tends to be relatively poorly absorbed while $\beta\text{-}Ca_3(PO_4)_2$ is more readily absorbed. The two can be combined (i.e. bi-phasic calcium phosphate) to form a mixture having characteristics somewhere between HA and $\beta\text{-}Ca_3(PO_4)_2$. A number of calcium containing compound combinations can be envisioned.

Sugars, Sugar Substitutes, Sweeteners, Carbohydrates and Equivalents

A salient aspect of a preferred embodiment is the incorporation of at least one sugar or sugar like substance to the bio-material matrix. Inventor discovered that some sugar containing bio-materials have significant osteoproliferative properties as well as enhanced adhesive capabilities. It is believed that a sugar like sucrose may be replaced or supplemented with other sugars and sugar related compounds.

Suitable sugars or sugar related compounds include but are not limited to sugary materials such as: sugars, sugar derivatives (i.e. sugar alcohols, natural and artificial sweeteners (i.e. acesulfame-k, alitame, aspartame, cyclamate, neohesperidine, saccharin, sucralose and thaumatin), sugar acids, amino sugars, sugar polymers glycosaminoglycans, glycolipids, sugar polymers, sugar substitutes including sugar substitutes like sucralose (i.e. Splenda®, McNeil Nutritionals LLC, Ft. Washington, Pa.), corn syrup, honey, starches, and various carbohydrate containing substances.

Exemplary sugars include but are not limited to: sucrose, lactose, maltose, cellobiose, glucose, galactose, fructose, dextrose, mannose, arabinose, pentose, hexose. Preferably the sugar additive is a polysaccharide, more preferably a disaccharide like sucrose. In one embodiment sugar combined with a flow agent like starch. An exemplary additive is approximately 97 weight percent sucrose and about 3 weight percent starch.

The sugar compound, like the other components, can be in a variety of forms including but not limited to dry forms (i.e. granules, powders etc.), aqueous forms, pastes, and gels. It may prove preferable to use a powdered form.

The inventor has shown that the invented sugar containing bio-material possess surprisingly good adhesive qualities. It is believed that the sugar may improve the physical (and possibly the chemical) bonding of the cement to objects.

Surprisingly and unexpectedly, it was discovered that the invented material and method provided spinal fusion without the need for additional fixation devices. This result was particularly surprising given recent studies showing the inability of calcium phosphate cements to provide spinal fusion.

It is believed that the osteoproliferative properties of other bio-materials may possibly be enhanced by the addition of certain sugars (as disclosed herein). The addition of sugar compounds to prior art and future bio-materials such as PMMA and/or phosphate based materials may enhance their bone stimulating characteristics.

Surprisingly and unexpectedly, the invention showed the ability to provide spinal fusion without the need for additional fixation devices which is particularly unexpected since previous calcium phosphate bone fillers/cements have not shown the ability to provide adequate spinal fusion.

Bone Graft Material

In one embodiment the composition of present invention provides a bone substitute and a platform for bone formation. An advantage of the substance is its gradual absorption by the body without rejection or reaction to contacted structures. A further advantage of the invented composition is its significant osteoproliferative properties. In fact, in studies the invented composition enhanced bone formation to such a surprising degree, so much so that it is believed that the composition may also be osteoinductive which is completely unexpected and unprecedented for a multi-purpose biomaterial without the use of growth factors. The bio-material is also believed to have micro and macro pores. Unexpectedly initial tests have shown that the invented composition is capable of providing spinal fusion.

Embodiments of the present invention have also been shown to have unique bonding characteristics suitable for fixation of various medical prosthesis.

Additional Embodiments

The formulations disclosed herein may incorporate additional fillers, additives and supplementary materials. The supplementary materials may be added to the bio-material in varying amounts and in a variety of physical forms, dependent upon the anticipated use. The supplementary materials can be used to alter the bio-material in various ways.

Supplementary materials, additives, and fillers are preferably biocompatible and/or bioresorbable. In some cases it may be desirous for the material to be osteoconductive and/or osteoinductive as well. Suitable biocompatible supplementary materials include but are not limited to: bioactive glass compositions, calcium sulfates, coralline, polyatic polymers, peptides, fatty acids, collagen, glycogen, chitin, celluloses, starch, keratins, nucleic acids, glucosamine, chondroitin, and denatured and/or demineralized bone matrices, and other materials, agents, and grafts (autografts, allografts, xenografts). Other suitable supplementary materials are disclosed in U.S. Pat. No. 6,331,312 issued to Lee and U.S. Pat. No. 6,719,992 issued to Constanz, which are hereby incorporated by reference in their entireties.

In another embodiment of the invention the bio-material contains a radiographic material which allows for the imaging of the material in vivo. Suitable radiographic materials include but are not limited to barium oxide and titanium.

In yet another embodiment the invented bio-material contains a setting retarder or accelerant to regulate the setting time of the composition. Setting regulators are preferable biocompatible. Suitable retarders include but are not limited to sodium chloride, sodium fluosilicate, polyphosphate sodium, borate, boric acid, boric acid ester and combination thereof.

The disclosed bio-material may also be prepared with varying degrees of porosity. Controlling porosity can be accomplished through a variety of means including: controlling the particle size of the dry reactants, and chemical and physical etching and leaching. A preferred embodiment increases porosity of the bio-material by addition of 1-20 weight percent of an aerating agent, preferably about 1-5 weight percent. Suitable aerating agents include but are not limited: carbonates and bicarbonates such as: calcium carbonate, sodium carbonate, sodium bicarbonate, calcium bicarbonate, baking soda, baking powder, and combinations thereof.

The biomaterial may be used as delivery system by incorporating biologically active compounds into the bio-material (i.e. antibiotics, growth factors, cell etc.). A porous bio-adhesive increases the effectiveness of such a delivery system.

Various antibiotics or other antibacterial and anti-viral compositions and agents can be added to the composition. The invented bio-material can act as a delivery device or the antibiotics can be added to protect against bacterial infection during surgery.

Cationic antibiotics, especially aminoglycosides and certain peptide antibiotics may be most desirable when incorporating drugs into the bio-material. Suitable aminoglycosides include but are not limited to: amikacin, butirosin, dideoxykanamycin, fortimycin, gentamycin, kanamycin, lividomycin, neomycin, netilmicin, ribostamycin, sagamycin, seldomycin and epimers thereof, sisomycin, sorbistin, spectinomycin and tobramycin. Using inorganic salts like sulfates, phosphates, hydrogenphosphates maybe preferable, sulfates being the most preferable. Further information about using antibiotics and growth factors in bio-materials can be found in U.S. Pat. No. 6,485,754, issued to Wenz, which is hereby incorporated by reference in its entirety. Growth factors include but are not limited to growth factors like transforming growth factor TGF-β. Vancomycin and similar antibiotics can also be used.

The disclosed bio-material composition may also be seeded with various living cells or cell lines. Any known method for harvesting, maintaining and preparing cells may be employed. See U.S. Pat. No. 6,719,993 issued to Constanz, U.S. Pat. No. 6,585,992 issued to Pugh and, U.S. Pat. No. 6,544,290 issued to Lee.

One embodiment of the invention has been shown to be extremely useful as a scaffold for hard tissue growth and possibly soft tissue growth as well. In addition, tissue-producing and tissue-degrading cells may be added to the composition included but not limited to: osteocytes, osteoblasts, osteoclasts, chondrocytes, fibroblasts, cartilage producing cells, and stem cells. Methods of isolating and culturing such cells are well known in the art.

The invented composition can incorporated into an orthopedic kit comprising: the material (i.e. MKP, metal oxide, calcium containing compounds etc.) in dry form, an activator solution (water or other aqueous solution), and any medical devices (i.e. syringes, knives, mixing materials, spatulas, etc.), implants, or other agents needed during an operation using the invented composition. The material and activator solution will preferably be present in a predetermined, optimized ratio. Other embodiments of such an orthopedic kit can also be envisioned. The biomaterial and other kit components are preferably sterilized by techniques well known in the art.

Having described the basic concept of the invention, it will be apparent to those skilled in the art that the foregoing detailed disclosure is intended to be presented by way of example only, and is not limiting. Various alterations, improvements, and modifications are intended to be suggested and are within the scope and spirit of the present invention. Additionally, the recited order of the elements or sequences, or the use of numbers, letters or other designations therefore, is not intended to limit the claimed processes to any order except as may be specified in the claims. Accordingly, the invention is limited only by the following claims and equivalents thereto.

All publications and patent documents cited in this application are incorporated by reference in their entirety for all purposes to the same extent as if each individual publication or patent document were so individually denoted.

The following is claimed as the present invention:

1. A method for fusing two adjacent vertebrae comprising:
accessing the intervertebral space defined between adjacent vertebrae;
mixing magnesia, potassium biphosphate, and a calcium phosphate with an aqueous solution forming an activated spinal fusion slurry (ASFS);
applying an effective amount of the ASFS to the intervertebral space between adjacent vertebrae;
allowing the ASFS to set forming a bonded vertebrae structure;
permitting bone growth into the bonded vertebrae structure providing fusion of the two adjacent vertebrae; wherein the ASFS promotes spinal fusion without the need for the fixation material BMP-2.

2. The method of claim 1, wherein the ASFS is applied to the transverse process.

3. The method of claim 1, wherein the ASFS has putty like consistency.

4. The method of claim 1, wherein the ASFS promotes spinal fusion without the need of any additional fixation devices and/or materials.

5. The method of claim 1, wherein the ASFS promotes spinal fusion without the need of the fixation material MPDH.

6. The method of claim 1, wherein the ASFS provides spinal fusion without the need for additional physical fixation devices.

7. The method of claim 1, wherein the applied ASFS is absorbed and replaced by bone over time.

8. The method of claim 1, wherein the ASFS initially provides structural strength and over time is replaced with new bone growth that fuses the vertebrae.

9. A method of providing spinal fusion comprising:
supplying a dry magnesium containing mixture comprising: magnesia, potassium biphosphate, and a tertiary calcium phosphate, wherein the weight percent ratio of potassium biphosphate to magnesia is between about 3:1 and 1:1;
mixing the dry magnesium containing mixture with an aqueous solution forming an activated spinal fusion slurry (ASFS);
applying an effective amount of the ASFS to a site between two vertebrae;
allowing the ASFS to set, forming a bonded vertebrae structure;
permitting bone growth into the bonded vertebrae structure providing fusion of the two adjacent vertebrae; wherein the ASFS promotes spinal fusion without the need for the fixation material BMP-2.

10. The method of claim 9, wherein the site between two vertebrae is the transverse process.

11. The method of claim 9, wherein the ASFS initially provides structural strength and over time is replaced with new bone growth that fuses the vertebrae.

12. A method to fuse vertebrae comprising:
supplying a dry magnesium containing mixture comprising: magnesia, potassium phosphate, and a tertiary calcium phosphate, wherein the weight percent ratio of potassium phosphate to magnesia is between about 3:1 and 1:1;

mixing the dry magnesium containing mixture with an aqueous solution forming an activated spinal fusion slurry (ASFS);

applying an effective amount of the ASFS to a site between two vertebrae;

allowing the ASFS to set, forming a bonded vertebrae structure;

permitting bone growth into the bonded vertebrae structure providing fusion of the two adjacent vertebrae; wherein the ASFS promotes spinal fusion without the need for the fixation material BMP-2.

13. The method of claim 12, wherein the site of application is the transverse process between two or more vertebrae.

14. The method of claim 12, wherein the dry mixture further comprises: a sugar compound.

15. The method of claim 12, where the dry mixture further comprises:

mono-sodium phosphate.

16. The method of claim 14, wherein the sugar compound selected from the group consisting of: sugars, sugar derivatives, sugar replacements and combinations thereof.

17. The method of claim 14, wherein the sugar compound is selected from a group consisting of: sugars, sugar alcohols, sugar acids, amino sugars, sugar polymers glycosaminoglycans, glycolipds, sugar substitutes and combinations thereof.

18. The method of claim 14, wherein the sugar compound comprises sucrose.

19. The method of claim 12, wherein the tertiary calcium phosphate is $Ca_{10}(PO_4)_6(OH)_2$.

* * * * *